(12) United States Patent
Sherman et al.

(10) Patent No.: US 7,928,739 B2
(45) Date of Patent: Apr. 19, 2011

(54) DEVICE FOR MEASURING MOISTURE IN SUBSTRATE AND HEALTH OF HAIR

(75) Inventors: Faiz Feisal Sherman, West Chester, OH (US); Vladimir Garstein, Cincinnati, OH (US); David Burton Moore, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/823,894

(22) Filed: Jun. 29, 2007

(65) Prior Publication Data

US 2008/0007273 A1 Jan. 10, 2008

Related U.S. Application Data

(60) Provisional application No. 60/818,173, filed on Jun. 30, 2006.

(51) Int. Cl.
*G01R 27/04* (2006.01)
(52) U.S. Cl. ............................. 324/640; 73/73
(58) Field of Classification Search .................... 324/640
See application file for complete search history.

(56) References Cited

U.S. PATENT DOCUMENTS

| | | | |
|---|---|---|---|
| 2,422,742 A | 6/1947 | Odessey | |
| 3,755,733 A | 8/1973 | Vankoughnett et al. | |
| 4,358,731 A | 11/1982 | Steinbrecher | |
| 4,361,801 A | 11/1982 | Meyer et al. | |
| 4,364,008 A | 12/1982 | Jacques | |
| 4,375,054 A * | 2/1983 | Pavio | 333/116 |
| 4,378,168 A | 3/1983 | Kuisma et al. | |
| 4,546,311 A | 10/1985 | Knöchel | |
| 4,744,154 A | 5/1988 | Bollinger et al. | |
| 4,834,968 A | 5/1989 | Bolich, Jr. | |
| 4,877,042 A | 10/1989 | Downey | |
| 5,256,978 A | 10/1993 | Rose | |
| 5,315,258 A | 5/1994 | Jakkula et al. | |
| 5,461,925 A | 10/1995 | Nguyen et al. | |
| 5,502,393 A | 3/1996 | Yamaguchi et al. | |
| 5,568,691 A | 10/1996 | Rubin | |
| 5,610,527 A | 3/1997 | Yamaguchi | |
| 5,767,409 A | 6/1998 | Yamaguchi | |

(Continued)

FOREIGN PATENT DOCUMENTS

EP 0176003 A1 4/1986

(Continued)

OTHER PUBLICATIONS

International Search Report, PCT/US2007/015157, dated Feb. 19, 2008 (7 pages).

(Continued)

*Primary Examiner* — Timothy J Dole
*Assistant Examiner* — Benjamin M Baldridge
(74) *Attorney, Agent, or Firm* — Angela K. Haughey; Laura R. Grunzinger

(57) ABSTRACT

A sensor for measuring moisture content of a substrate, comprising:
- a coplanar waveguide;
- a directional coupler having a pair of generally parallel first and second strips defining a coupling gap therebetween; and
- a high frequency signal generator electrically coupled to said first strip and operable to couple power to said second strip with the substrate placed across said coupling gap to thereby generate a coupled power signal in said second strip having an amplitude related to moisture content of the substrate.

3 Claims, 11 Drawing Sheets

U.S. PATENT DOCUMENTS

| | | | |
|---|---|---|---|
| 5,767,685 A | 6/1998 | Walker | |
| 5,857,379 A | 1/1999 | Lulofs et al. | |
| 5,864,240 A | 1/1999 | Hirai et al. | |
| 5,969,254 A | 10/1999 | Yamaguchi | |
| 6,040,282 A | 3/2000 | Guskey et al. | |
| 6,237,417 B1 | 5/2001 | Lonsdale et al. | |
| 6,248,317 B1 | 6/2001 | Snyder et al. | |
| 6,327,899 B1 | 12/2001 | Diekhans et al. | |
| 6,490,492 B1 | 12/2002 | Fertig et al. | |
| 6,854,322 B2 | 2/2005 | Sherman et al. | |
| 7,261,000 B2 | 8/2007 | Sherman et al. | |
| 2001/0030543 A1* | 10/2001 | Joshi et al. | 324/643 |
| 2003/0045262 A1* | 3/2003 | Vaughan | 455/323 |
| 2003/0226397 A1* | 12/2003 | Sherman et al. | 73/73 |
| 2004/0194541 A1* | 10/2004 | Sherman et al. | 73/73 |
| 2005/0120779 A1* | 6/2005 | Sherman et al. | 73/73 |

FOREIGN PATENT DOCUMENTS

| | | |
|---|---|---|
| EP | 0082560 B1 | 3/1987 |
| EP | 0701118 A2 | 3/1996 |
| EP | 0902276 A2 | 3/1999 |
| EP | 0926487 A1 | 6/1999 |
| EP | 0619485 B1 | 12/1999 |
| EP | 0990887 A2 | 4/2000 |
| EP | 0792113 B1 | 12/2001 |
| JP | 51125567 A2 | 11/1976 |
| JP | 54136972 A2 | 10/1979 |
| JP | 57163860 | 10/1982 |
| JP | 58211624 A2 | 12/1983 |
| JP | 58215546 | 12/1983 |
| JP | 59018455 | 1/1984 |
| JP | 59126943 | 7/1984 |
| JP | 60198449 | 10/1985 |
| JP | 61194341 | 8/1986 |
| JP | 61195341 | 8/1986 |
| JP | 61221639 | 10/1986 |
| JP | 61221640 | 10/1986 |
| JP | 61221641 | 10/1986 |
| JP | 61221642 | 10/1986 |
| JP | 61251756 | 11/1986 |
| JP | 61251759 | 11/1986 |
| JP | 63075562 | 4/1988 |
| JP | 63163143 A | 7/1988 |
| JP | 2283313 A2 | 11/1990 |
| JP | 3195508 A2 | 8/1991 |
| JP | 04-038463 | 2/1992 |
| JP | 04-058903 | 2/1992 |
| JP | 04-193203 | 7/1992 |
| JP | 04-336002 | 11/1992 |
| JP | 05-007508 | 1/1993 |
| JP | 05-095813 | 4/1993 |
| JP | 5184420 A1 | 7/1993 |
| JP | 5192216 | 8/1993 |
| JP | 5192217 | 8/1993 |
| JP | 5196506 | 8/1993 |
| JP | 5293010 | 11/1993 |
| JP | 7088009 | 4/1995 |
| JP | 11322547 A2 | 11/1999 |
| JP | 2003-254926 | 9/2003 |
| SU | 1453275 A | 1/1989 |
| WO | WO-86/01696 A1 | 3/1986 |
| WO | WO-95/02815 A1 | 1/1995 |
| WO | WO-97/09898 A1 | 3/1997 |
| WO | WO-00/15073 A1 | 9/1999 |
| WO | WO-03/104782 A1 | 12/2003 |

OTHER PUBLICATIONS

Matsuda, K. et al., "High-Q Active Inductor and Its LC Oscillator Application," Technical Report of IEICE, Tokyo, Japan, vol. NPL2001-39, pp. 37-41 (Jul. 2001) Abstract, XP-009042395, Abstract Only.

Abrosimova, E.B. et al., "Amplitude UHF Humidity Meter for Solid and Powdered Materials," Measurement Techniques, vol. 39, No. 11, Nov. 1, 1996, pp. 1162-1165.

Kupfer, K. et al., "Materialfeuchtemessung mit Mikrowellen (Moisture Measurement with Microwaves)," Technisches Messen TM, R. Oldenbourg Verlag, Munchen, Germany, vol. 59, No. 3, Mar. 1, 1992, pp. 110-115, Abstract Only.

Ghorpade R. et al., "Response of Thick and Thin Film [lambda]/2 Microstrip Rejection Filter to Leaf Moisture," Radio Science American Geophys. Union USA, vol. 41, No. 2, Mar. 2006, (10 pages) XP009095530.

K. Vijaya et al., "Effect of Bulk and Thin Film Dielectric Overlay on the Characteristics of Microstriplines," Bull. Mater. Sci., [Online], vol. 8, No. 3, Jun. 1986, pp. 397-405, XP002467902.

Maxim: "Introduction to Common Printed Circuit Transmission Lines," Application Note 2093, Jun. 2, 2003 (6 pages).

* cited by examiner

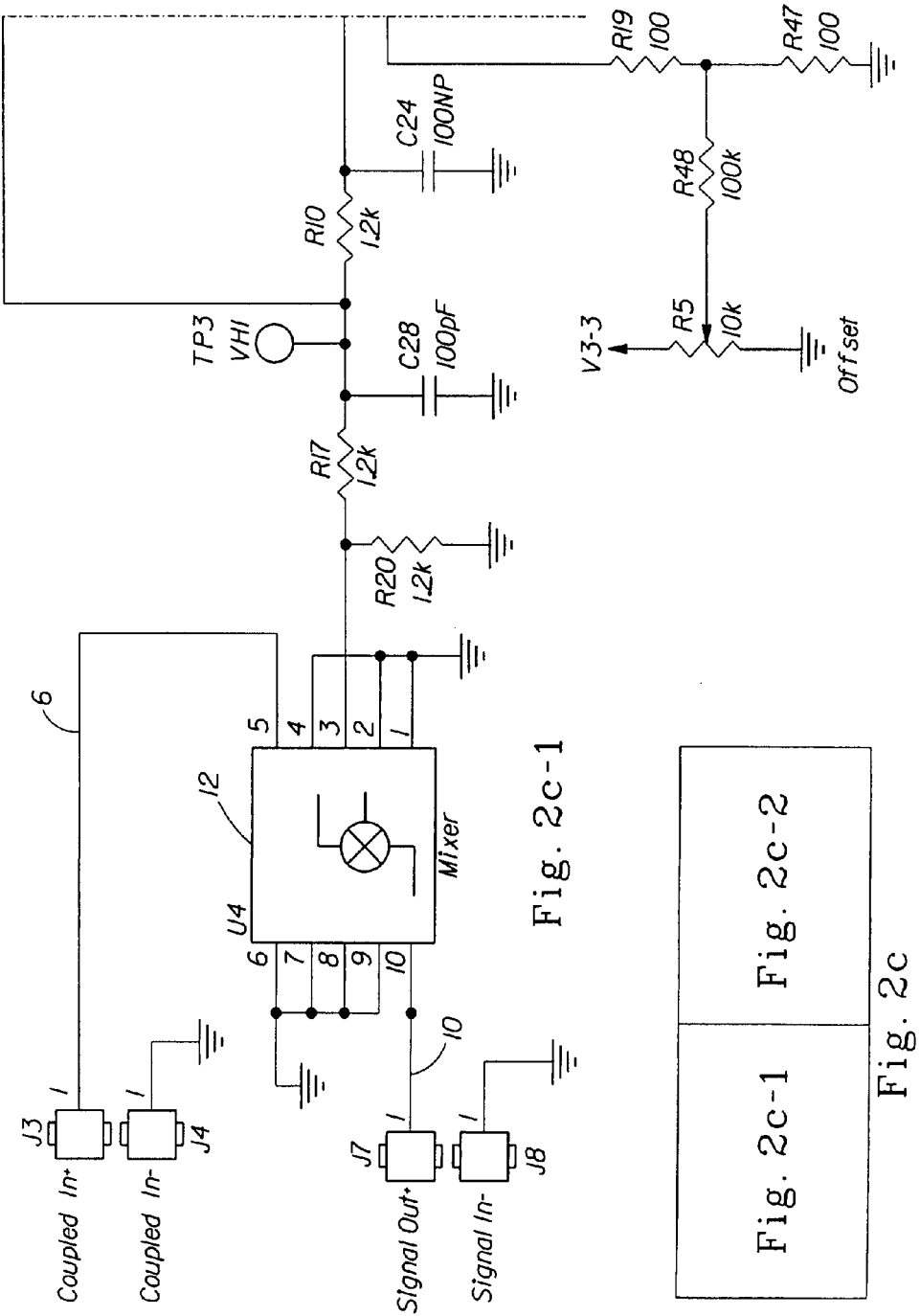

DEVICE FOR MEASURING MOISTURE IN SUBSTRATE AND HEALTH OF HAIR

CROSS REFERENCE TO RELATED APPLICATION

This application claims the benefit of U.S. Provisional Application No. 60/818,173, filed Jun. 30, 2006.

FIELD OF THE INVENTION

The present invention relates generally to measurement sensors and, more particularly, to a sensor for measuring a property of a substrate, such as the internal and external moisture content of biological systems such as hair.

BACKGROUND OF THE INVENTION

Many substrates are hydroscopic and permeable which means that they will absorb water from the environment. For example, under normal conditions, water accounts for about 12% to about 15% of the composition of hair. Normal hair can absorb more than 30% of its own weight in water. If the hair is damaged it has less ability to retain water within the hair fibers which gives hair its healthy appearance. It is therefore important to be able to accurately measure hair moisture to determine the overall health of hair or point of moisture in hair that offers best styling condition.

Moisture sensing devices have been developed in the past to determine the moisture level in substrates, and have relied on various techniques including resistance and capacitance measurements to obtain the desired indication. However, these methods only work well for a known cross sectional quantity and density of the substrate being measured. As the substrate density or compactness is varied, these measurement techniques fail. Additionally, these techniques rely primarily on the moisture content outside of the substrate fiber for the measurement, and do not have the ability to accurately measure moisture content within substrate fibers as well.

Other disadvantages of previous devices are that the sensor and circuit components are not coplanar. Previous devices have incorporated a coaxial cable to interconnect sensor and circuit components. This, in particular, poses difficulty in packaging the system into a hand held enclosure. In turn, it also results in increasing package costs and lower sensitivity.

Thus, there is a need for an integrated sensing device with increased sensitivity, which can accurately and reliably determine the moisture content of a substrate, such as hair, including moisture both inside and outside of the hair fiber.

SUMMARY OF THE INVENTION

The present invention overcomes the foregoing and other shortcomings and drawbacks of moisture sensors and methods of determining moisture content heretofore known. While the invention will be described in connection with certain embodiments, it will be understood that the invention is not limited to these embodiments. On the contrary, the invention includes all alternatives, modifications and equivalents as may be included within the spirit and scope of the present invention.

One embodiment comprises a sensor for measuring moisture content of a substrate, comprising:
a coplanar waveguide;
a directional coupler having a pair of generally parallel first and second strips defining a coupling gap therebetween; and
a high frequency signal generator electrically coupled to said first strip and operable to couple power to said second strip with the substrate placed across said coupling gap to thereby generate a coupled power signal in said second strip having an amplitude related to moisture content of the substrate.

Another embodiment of the present invention comprises a sensor for measuring moisture content of a substrate, comprising:
a directional coupler having a pair of generally parallel first and second strips defining a coupling gap therebetween; and
a high frequency signal generator electrically coupled to said first strip and operable to couple power to said second strip with the hair placed across said coupling gap to thereby generate a coupled power signal in said second strip having an amplitude related to health of the hair, wherein said second strip comprises an AC/DC detector which is operable to generate an output voltage signal having a value related to moisture content of the substrate.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

While the specification concludes with claims that particularly point out and distinctly claim the invention, it is believed the present invention will be better understood from the following description.

The present system for measuring moisture in and on a substrate comprises a sensor for measuring moisture which is connected to a circuit by a coplanar waveguide. Each these essential components, as well as preferred or optional components, are described in detail hereinafter.

Referring now to the Figures and to FIGS. 1, 2A-2F and 3A, in particular, a directional coupler sensor 1 is shown in accordance with the principles of the present invention. For the sake of simplicity, the sensor 1 will be described herein in connection with measuring the moisture content of hair. However, it will be appreciated by those of ordinary skill in the art that the present invention has use in a wide variety of applications and is therefore not limited to the analysis of hair or the measurement of moisture content in a substrate. Rather, the sensor 1 of the present invention is readily adaptable to analyze a wide variety of substrates and to measure different moisture related properties of those substrates as will be readily appreciated by those of ordinary skill in the art. Non-limiting examples of suitable substrates for use with the sensor of the present invention include hair, skin, wood, synthetic and non synthetic fibers, mix fibers, polymeric surfaces, and similar materials.

For example, in the measurement of the moisture content of a substrate, the sensor 1 operates under the principle that as the moisture content of a substrate increases, so does its effective relative signal coupling. As will be described in greater detail below, the sensor 1 is designed to measure the relative signal coupling induced by a substrate, and from that measurement of the coupled signal, the moisture content of the substrate can be determined. The moisture content value may be presented on a visual display, indicated through a user-perceptible audible tone and/or used as a control signal to control a function of a device. More preferably, the indicator is one or more LED lights.

Figure 1:
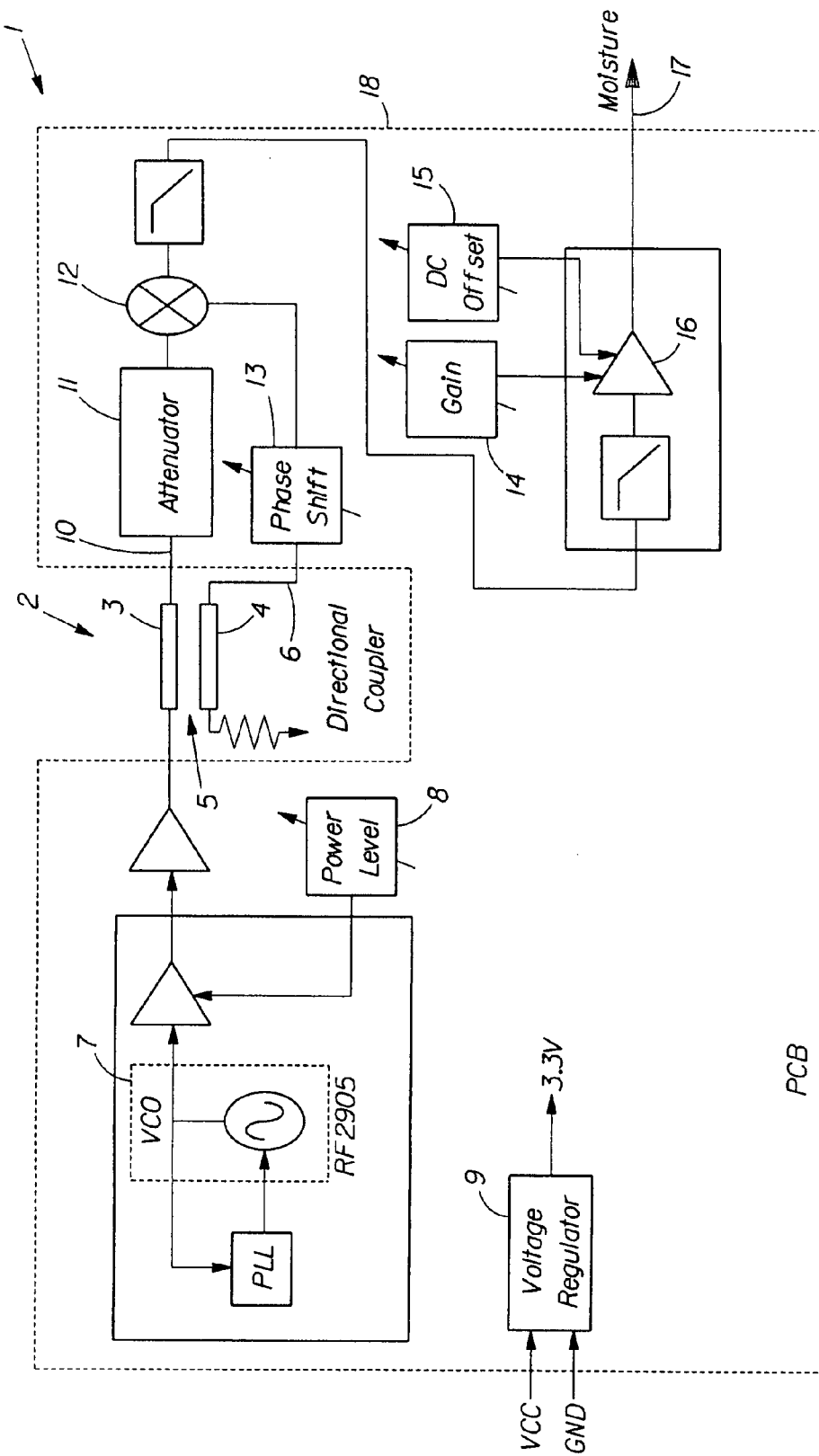
FIG. 1 is a functional block diagram of a directional coupler sensor in accordance with the principles of the present invention.
Figures 1, 2A:
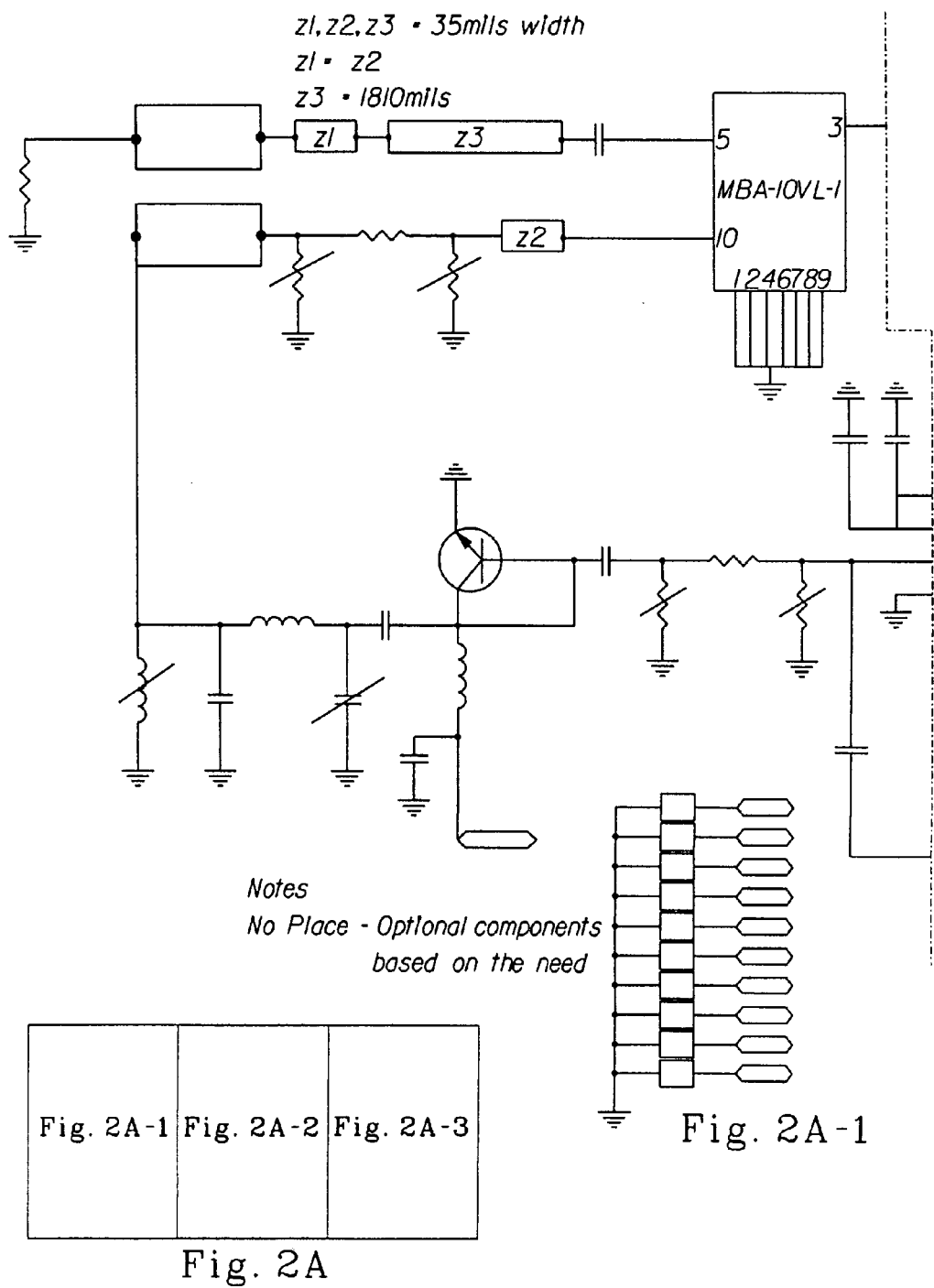
FIG. 2A includes FIGS. 2A-1, 2A-2, and 2A-3, and is a circuit representation of a directional coupler sensor in accordance with the principles of the present invention.
Figures 2, 2A:
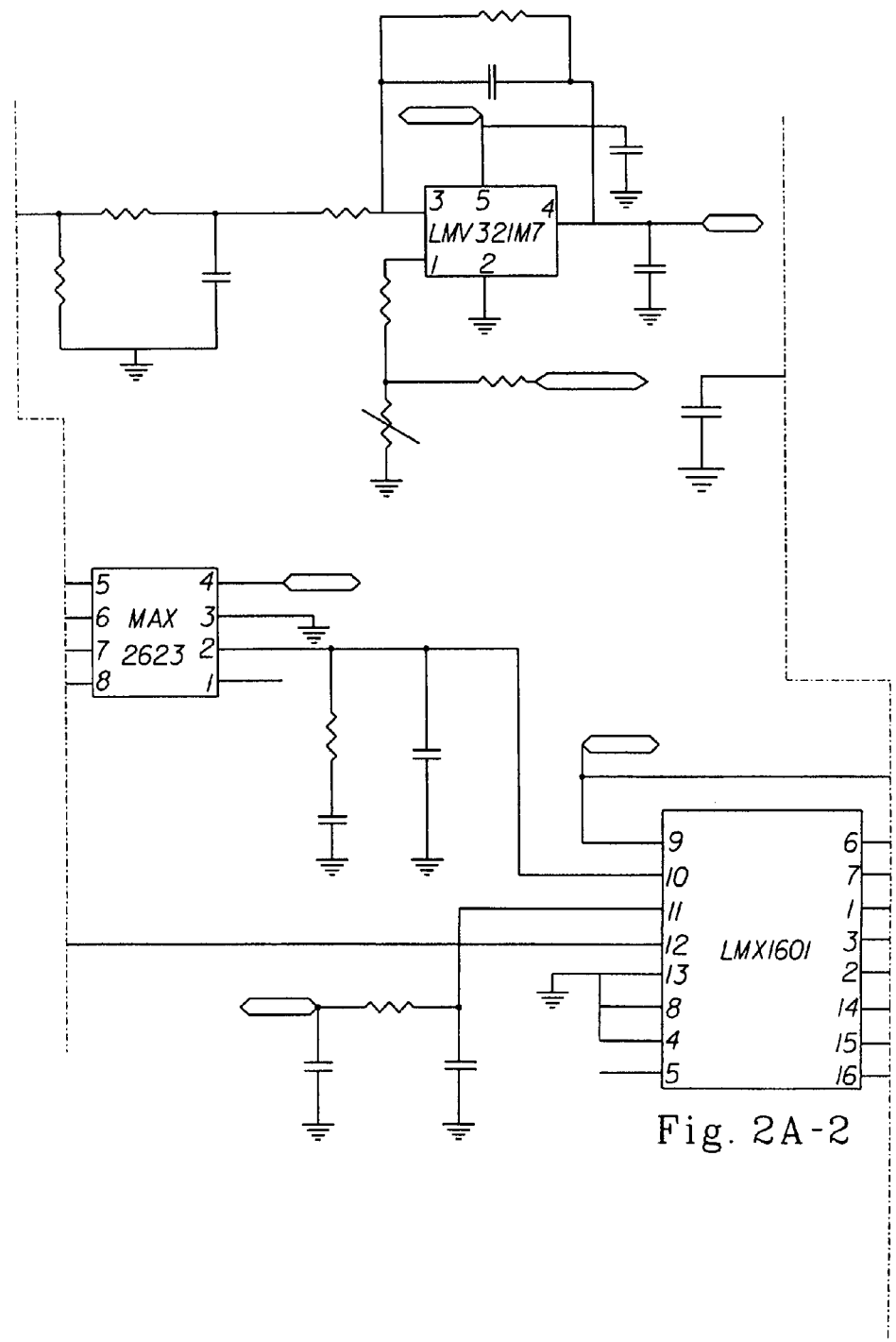
Figures 2, 2A, 3:
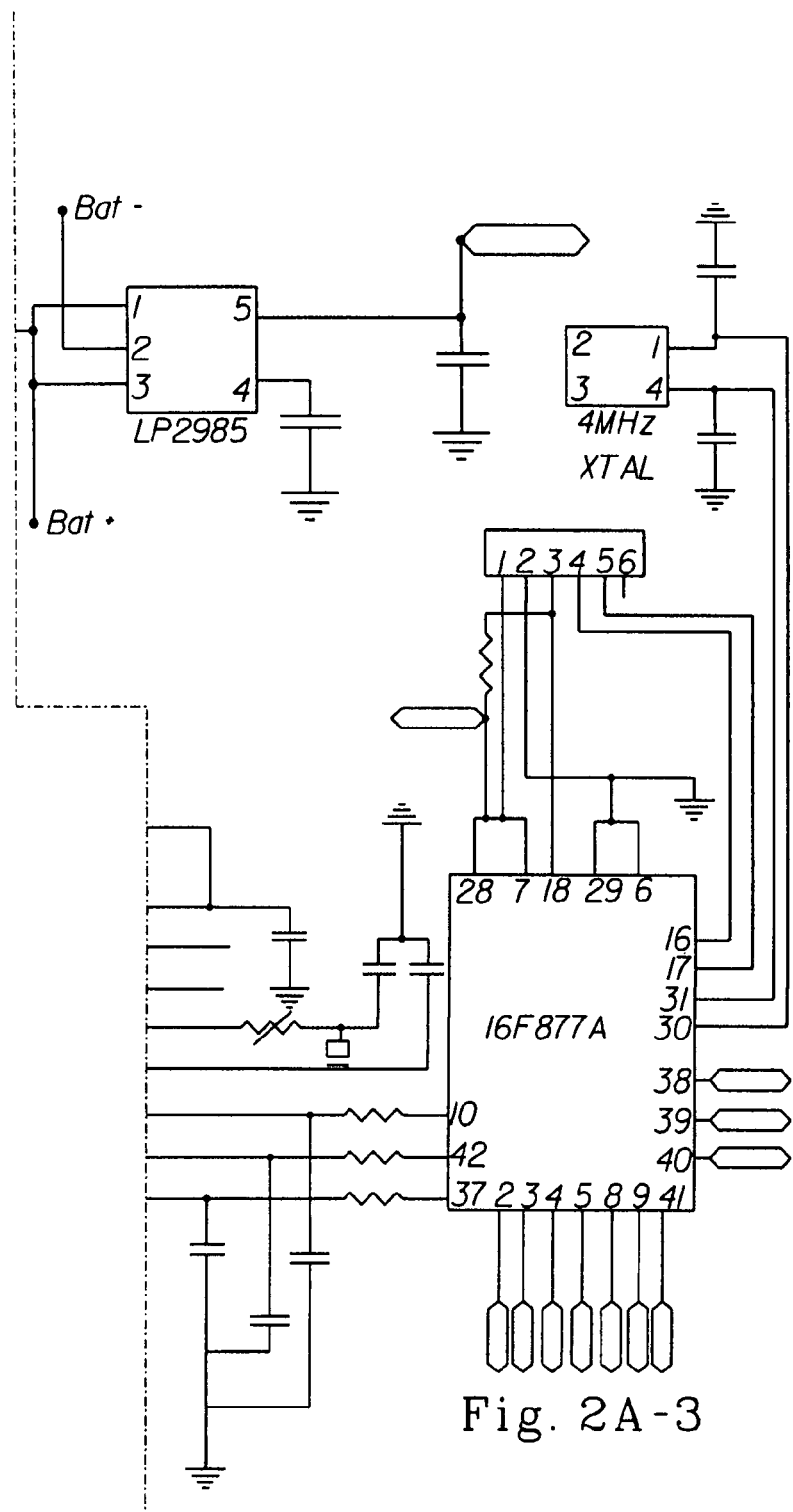
Figure 2B:
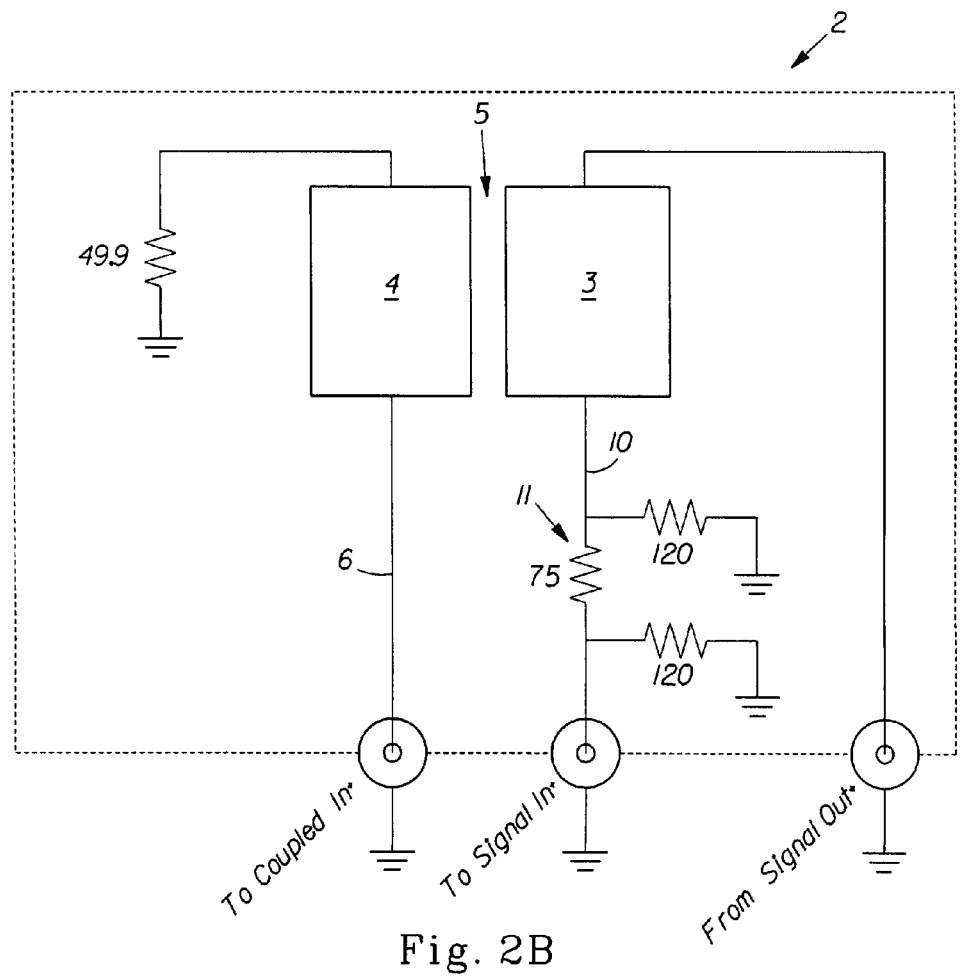
FIG. 2B is a circuit representation of a directional coupler for use in the sensor of FIG. 1 in accordance with one embodiment of the present invention.
Figures 2, 2C:
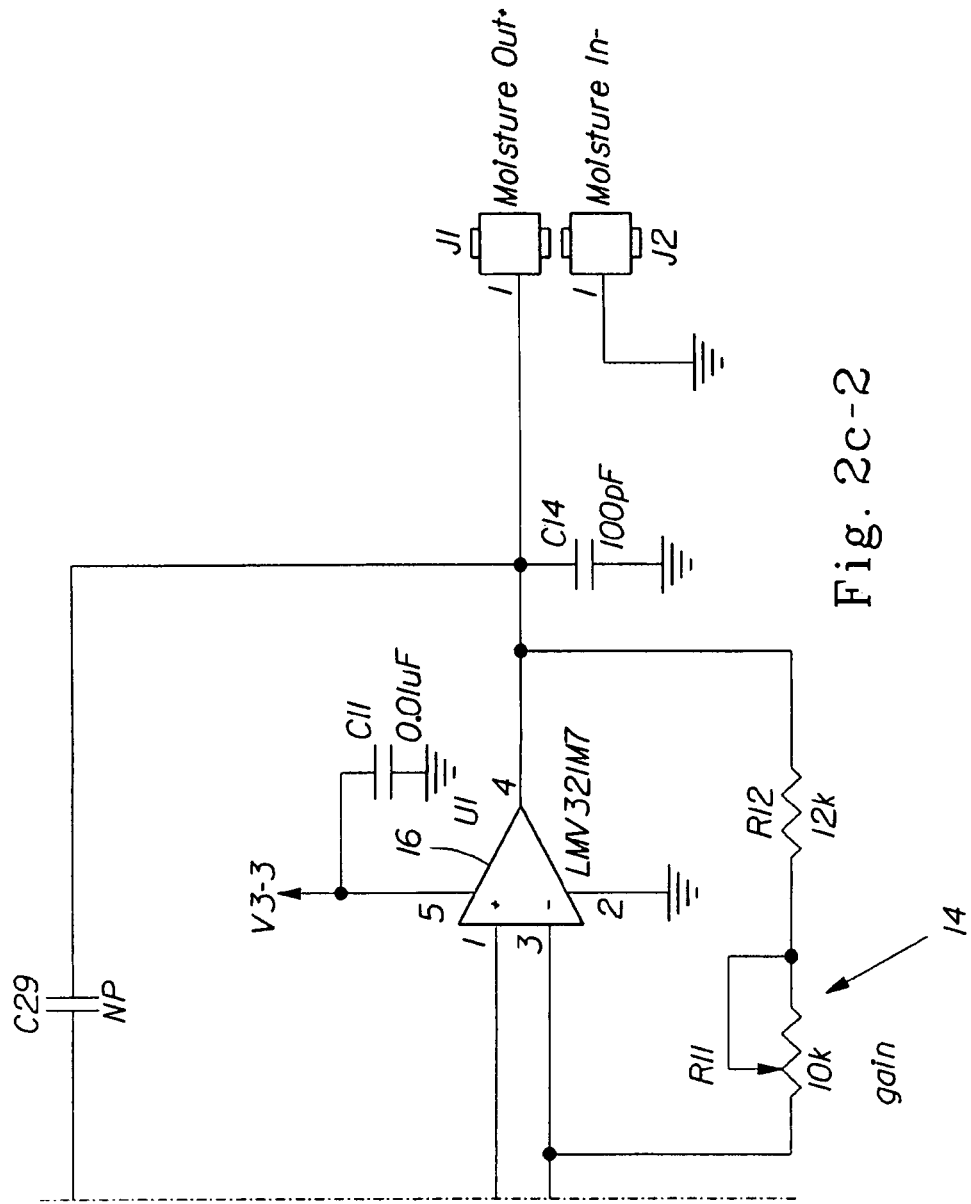
FIG. 2C includes FIGS. 2C-1 and 2C-2, and is a circuit representation of a moisture content detector for use in the sensor of FIG. 1 in accordance with one embodiment of the present invention.
Figure 2D:
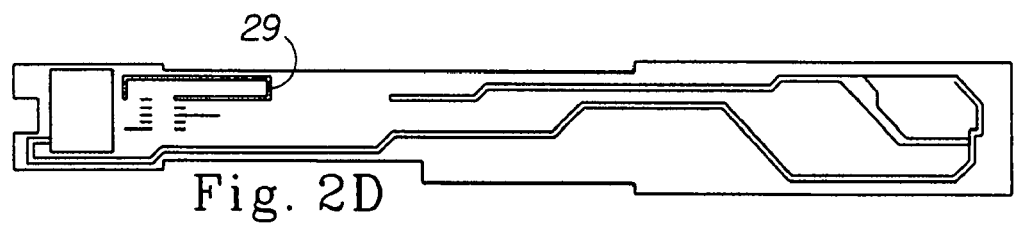
FIG. 2D is a circuit representation of the top layer of the PCB layout.
Figure 2E:
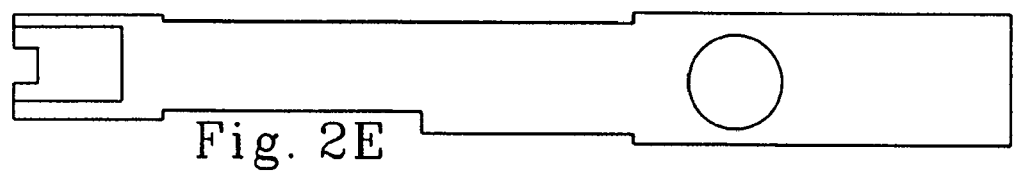
FIG. 2E is a circuit representation of the middle layer of the PCB layout (Ground Plane)

As shown in FIGS. 1, 2A-2F and 3A, the sensor 1 incorporates a high frequency directional coupler 2 having a pair of generally parallel strips 3 and 4 that define a coupling gap 5 therebetween. The term "couple," as used herein, means to position two electric circuit components close enough to permit an exchange or electromagnetic energy from one to another. In one embodiment, the parallel strips 3, 4 are supported on an FR4 printed circuit board (PCB) 18 (FIGS. 2D-3B) having a ground plane 19 formed on a lower surface of the board 18. In one embodiment, the height "h" of the PCB 18 is 0.062 in., each strip 3, 4 has a width "w" of 0.17 in. and a length "1" of 0.350 in., and the coupling gap 5 has a gap distance "s" of 0.020 in. Of course, it will be appreciated by those of ordinary skill in the art that other dimensions of the PCB 18, strips 3, 4 and gap 5 are possible as well, depending on a particular application, as will be described in detail below. Also, the ground plane 19 does always have to be in the bottom of the PCB but can also be in the middle as shown in FIG. 2E.

A high frequency signal generator 7 is electrically coupled to strip 3 and is operable to generate an electromagnetic field across the coupling gap 5 that couples power to strip 4 with the substrate placed across, i.e., generally normal to the longitudinal axis of, the coupling gap 5 in a packed manner as will be described in detail below. Strip 4 may also comprise an AC/DC detector (not illustrated) which is operable to generate an output voltage signal which has a value related to the moisture content of the substrate. The presence of the AC/DC detector obviates the need for the mixer 12 component. The signal generator 7 generates a coupled power signal in the coupled strip 3 that has an amplitude related to the moisture content, of the substrate placed across the coupling gap 5. The signal generator 7 is phase locked to maintain frequency and measurement accuracy, stability, and repeatability, and has an adjustable power. The signal generator 7 is preferably operable to generate signals in the VHF to UHF frequency ranges, i.e., between about 30 MHz and about 3 GHz, although other frequency ranges are possible as well. In accordance with one embodiment, the signal generator 7 may operate at about 1 GHz, such as at about 915 MHz, since it is contemplated that the water content of a substrate may be most accurately determined by its measured impedance in the near GHz range.

In accordance with one embodiment, the sensor 1 utilizes the reverse power coupling variation of the high frequency directional coupler 2 (FIG. 2B) to measure the change in the impedance of the material placed across the coupling gap 5. As the substrate is packed across the coupling gap 5, the directional coupler 2 becomes mismatched, and this mismatch causes a monotonic increase in the reverse power coupling of the directional coupler 2 as the impedance across the gap 5 is increased as the result of increased moisture content of the material. The amplitude of the reversed power in the reverse power leg 6 (FIGS. 1 and 2B) from strip 4 is generally a direct measure of the impedance, and hence the moisture content, of the substrate placed across the coupling gap 5. As will be described in detail below, the moisture content of the substrate, i.e., its water content by weight, can be determined from the measured impedance of the sample.

Further referring to FIGS. 1, 2A-2F, the forward power signal from strip 3 is electrically coupled to one port of a mixer 12 (example of which can be a MBA-10VL-1 shown in FIG. 2A) through a forward power leg 10 (FIGS. 1 and 2B) and, optionally, an attenuator 11. For example, the forward power signal may optionally be attenuated to about −10 dBm by the attenuator 11. However, the attenuator 11 is not essential because the coplanar waveguide (discussed below) provides excellent control of DC off-set hence increasing dynamic range. The coupled power signal from strip 4 is phase shifted by a phase shifter 13 and is electrically coupled to another port of the mixer 12 through the reverse power leg 6. The phase shift is made possible via a coplanar waveguide. As used herein, "coplanar" means that the waveguide is integrated into the main PCB 18 of the device and without using coaxial cable connections (i.e., FIGS. 2D-2F). The mixer 12 may act as a coherent receiver in that it is most responsive to coupled signals that, are in phase with the forward power signal. The phase shifter 13 assures the proper phase coherence of the reverse power signal relative to the forward power signal for the mixer 12 to produce the maximum discernable mixer output. With the mixer forward power set to the appropriate level through the adjustable power 8, the output of the mixer 12 monotonically increases with an increase in the reverse coupled power which is caused by increase in substrate moistures content. The mixer 12 demodulates or reduces to DC base band the value of the coupled power though the directional coupler 2. The DC output of the mixer 12 is filtered and amplified by amplifier 16 to produce a measurable output voltage that is related to the moisture content 17 of the substrate placed across the gap 5. The amplifier 16 includes an adjustable gain 14 and an adjustable DC offset 15.

In one embodiment, the sensor-circuit interconnection is made by a 50 ohm coplanar waveguide. The waveguide trace 29 is depicted in FIG. 2D. The coplanar design provides for ideal phase correction control with minimal signal loss of the sensor. The system is typically powered by a regulated 3.3 V power supply. The voltage regulator 9 regulates power for the integrated circuit. FIGS. 1 and 2A show the block and schematic diagrams respectively of an embodiment of the PCB design. The RF signal generator 7 propagates a signal to the sensor using a phase locked loop (PLL) circuit. The PLL block works with an external voltage controlled oscillator (VCO) which is electrically coupled to it. One of ordinary skill would be familiar with such signal generators. The PLL can be programmed digitally. And hence, its frequency and the power level can be adjusted by the program. Since the maximum power output of the chip is insufficient, a single transistor amplifier 16 is used to further amplify the signal. However, the PLL is communicated with via an I2C protocol. Hence, in one embodiment, a microcontroller is used to communicate with the PLL using I2C logic. A high level C language is used to write the entire function of the system. The C program is then converted into machine code for the microcontroller using an HT-PIC compiler and a MPLAB tool to download the machine code to the microcontroller. The PLL circuit used can be seen in FIG. 2A. The power of the RF signal generated out of the VCO is about −4 dBm. Hence, the signal is amplified to feed a 0 dBm signal strength onto the sensor. A single transistor RF amplifier 16 is used to amplify the signal to 0 dBm. Coupled micro strips 3, 4 are used for the sensor to detect the moisture present in the object being tested. The coupled signal is fed into the mixer RF input and the reference signal is fed into the LO port of a mixer circuit 12 (MBA-10VL). Super heterodyne principle is used to enhance the noise immunity of the system; the principle equation that governs super heterodyne principle is explained by equations (1)-(3) below.

$$V0 = A_1 \cos(\omega_1 t) \cdot A_2 \cos(\omega_2 t) \quad (1)$$

$$V0 = \frac{A_1 A_2}{2}[\cos(\omega_1 - \omega_2)t + \cos(\omega_1 + \omega_2)t] \quad (2)$$

After passing through the low pass filter, the final output voltage becomes, $$V0 = \frac{A_1 A_2}{2} \quad (3)$$

Equation (3) is valid, if the input signal frequency at local oscillator (LO) and Radio frequency (RF) port are the same.

The mixer 12 is a negative polarity detector (i.e., for a zero phase difference between the inputs, the output voltage is negative). Zero phase difference inputs are used to obtain the maximum output of the mixer 12. The high frequency component of the mixer 12 is filtered and the dc output is fed into an operational amplifier 16 based amplification circuit. The amplification of the circuit is kept at around gain of 200. A positive offset null circuit is used to eliminate any possible offset in the mixer 12 output.

PCB Layout Design

The top layer of the PCB FIG. 2D is used for component placement. Top and bottom layers are used for signal routing. The middle layer FIG. 2E is used specifically for ground connection and it is placed at 5 mm below the top layer. This spacing is very important for 50 ohm matching of the coplaner waveguide dimension.

Sensor and Waveguide Design

Sensor and waveguide designs are very critical, because this design determines the performance of the entire system. Better sensor design and phase matching provides better sensitivity while 50 ohm matched waveguide design provides for lowest signal loss.

Figure 2F:
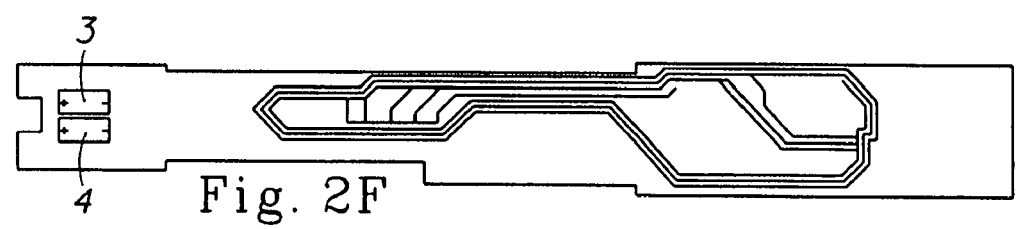
FIG. 2F is a circuit representation of the bottom layer of the PCB layout.
Figure 2G:
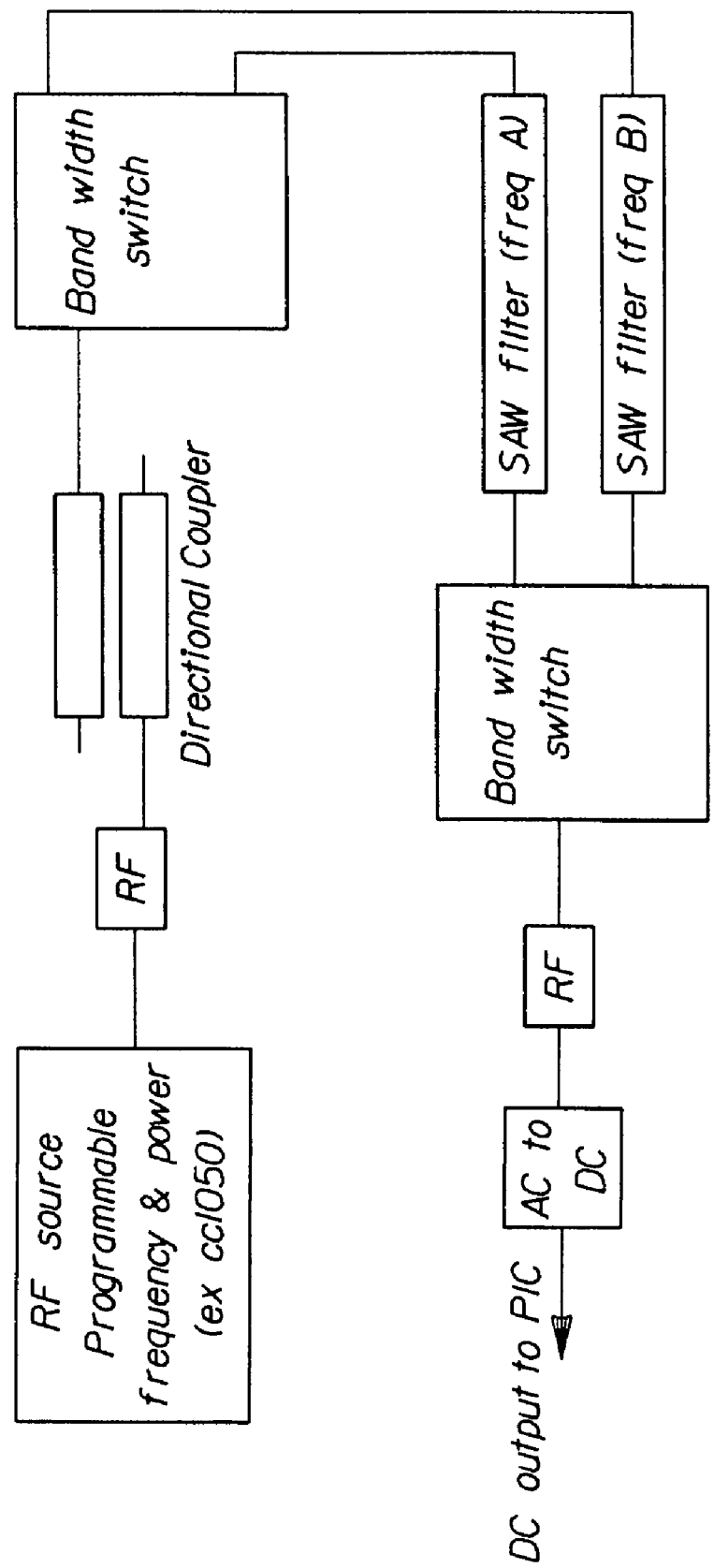
FIG. 2G is a block representation of the directional coupler sensor configuration.
Figure 3A:
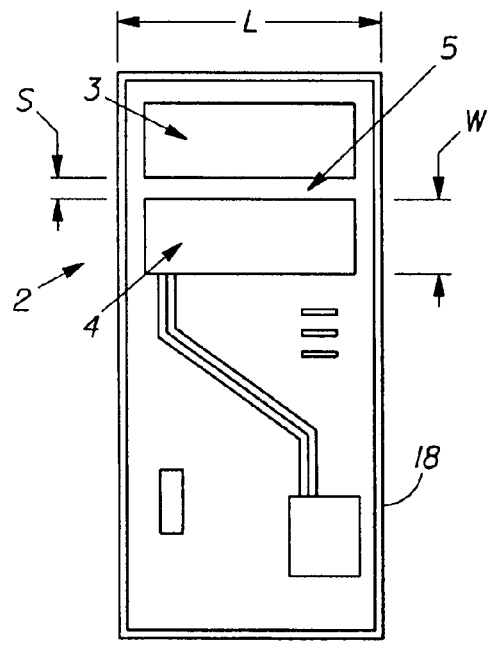
FIG. 3A is a top plane view of the sensor of FIG. 1 shown integrated onto a printed circuit board.
Figure 3B:
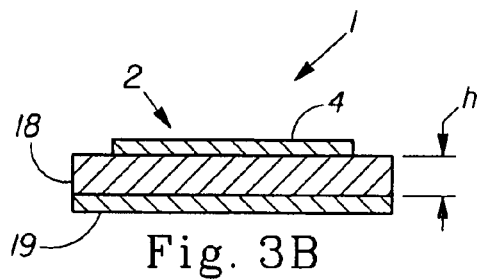
FIG. 3B is a cross-sectional view of FIG. 3A.

FIGS. 2D, 2F, and 3 show an embodiment of the sensor and waveguide design. Sensitivity of the sensor increases by increasing the space between the strips 3, 4 however by doing so, the coupling signal level goes well below −50 dBm. At such a low-level signal, the signal-to-noise ratio reduces drastically. Hence, in an embodiment, the sensor spacing is fixed at 0.020 inches with a good signal to noise ratio (SNR). Sensitivity also increases by decreasing the dielectric constant of the board material. Typically Rogers boards are more sensitive than FR4 type boards. Both FR4 and Rogers boards are readily available from the Rogers Corporation.

For the waveguide design on a FR4 PCB material (3 layer board with top to middle layer spacing=5 mm), the w/d ratio is equal to 1.8.

"w" is the width of the trace and "d" is the distance between the trace and the ground plane. In a preferred embodiment, the trace 29 width and lengths are designed to match 50Ω input impedance of the mixer. This 50Ω matching is very important for the lossless signal transmission. The calculations for determining the width and length of the microstrip lines are done using the generalized equations (5)-(8) mentioned below:

For w/d≦2:

$$\frac{w}{d} = \frac{8e^A}{e^{2A} - 2} \quad (5)$$

Where

"w" is width of the microstrip, and "d" is the distance between the microstrip and the ground plane $$A = 2\pi \frac{Z_0}{Z_f} \sqrt{\frac{\varepsilon_r + 1}{2}} + \frac{\varepsilon_r - 1}{\varepsilon_r + 1}\left(0.23 + \frac{0.11}{\varepsilon_r}\right) \quad (6)$$

Where $Z_0$ is the impedance that is to be matched (in this case it is 50 ohms) and $\varepsilon_r$ is the relative permittivity of the material (for FR4, it is 4.7)

For w/d>2:

$$\frac{w}{d} = \frac{2}{\pi}\left\{B - 1 - \ln(2B - 1) + \frac{\varepsilon_r - 1}{2\varepsilon_r}\left[\ln(B - 1) + 0.39 - \frac{0.61}{\varepsilon_r}\right]\right\} \quad (7)$$

Where factor B is $$B = \frac{Z_f \pi}{2Z_0 \sqrt{\varepsilon r}} \quad (8)$$

Where $Z_f$ is the wave impedance in free space (i.e., 376.8Ω)
For a preferred system designed on FR4 board material, the specifications available are
Dielectric constant $\varepsilon_r$=4.7
Board thickness top-to-bottom layer=0.062 inches
Board thickness top-to-ground layer=0.0196 inches
Characteristic impedance $Z_0$=50 Ω
Inserting all the above parameters in equation (5) gives w/d=1.8, hence for a height of 0.0196 inches, w is approximately equal to 0.0350 inches.
Calculations for 90° phase shift
Required Φ=90°
Φ=β1

Where, β is the propagation constant and l is the required length for 90° phase shift.
Where, $$k_0 = \frac{2\pi f}{c} = 715.748 \text{ in}^{-1} \text{ and}$$

$\varepsilon_e$ = effective dielectric constant $$= \frac{\varepsilon_r + 1}{2} + \frac{\varepsilon_r - 1}{2} + \frac{1}{\sqrt{1 + 12d/w}}$$

$$= 3.52,$$

and $\varepsilon_r$ is the relative dielectric constant (for FR4 board, it is 4.7)
Where, f is the frequency of operation, and c is the velocity of light in free space.

$$l = \frac{90(\pi/180)}{18.18\sqrt{3.52}} = 1.810 \text{ inches}$$

Therefore, based on the above calculation, the length of the waveguide trace 29 is 1.810 inches in order to achieve a phase match at the mixer 12 input.

Figure 4A:
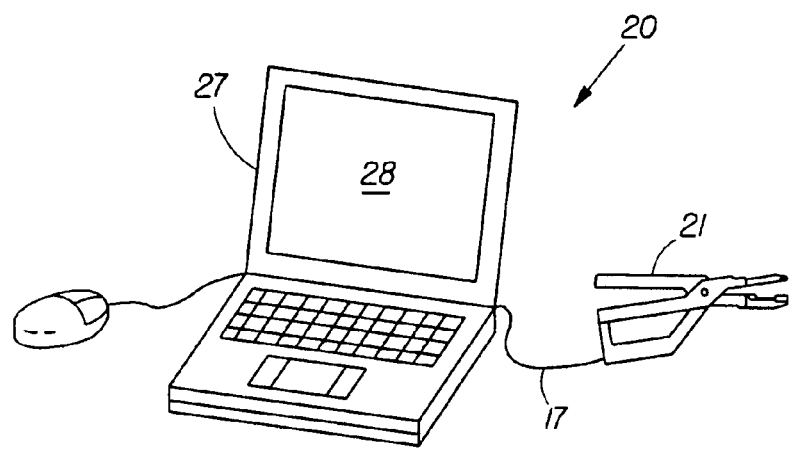
FIG. 4A is a perspective view of a directional coupler sensor system in accordance with one embodiment of the present invention.
Figure 4B:
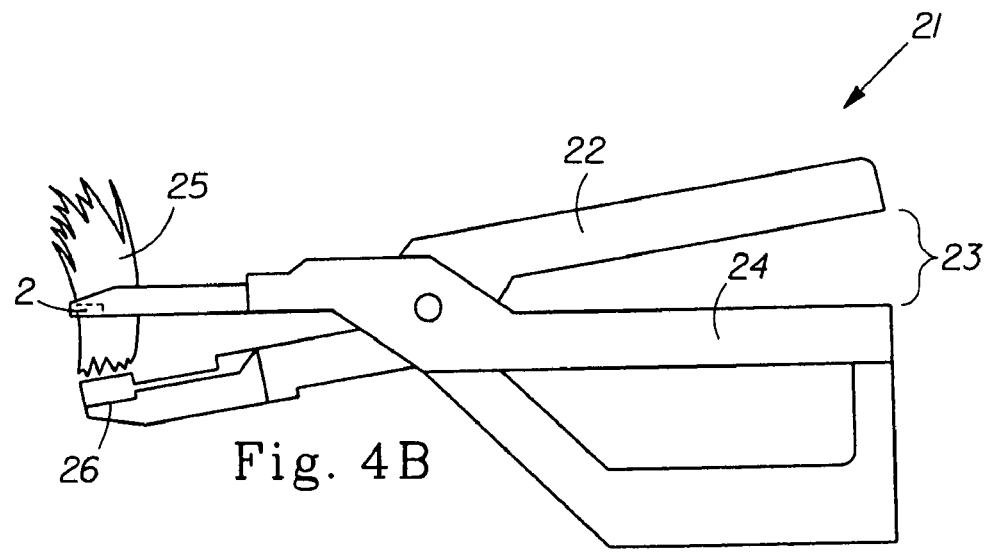
FIG. 4B is an enlarged front elevational view of a hair clamping device for use in the sensor system of FIG. 4A, illustrating the clamping device in an open position to receive hair in the device.
Figure 4C:
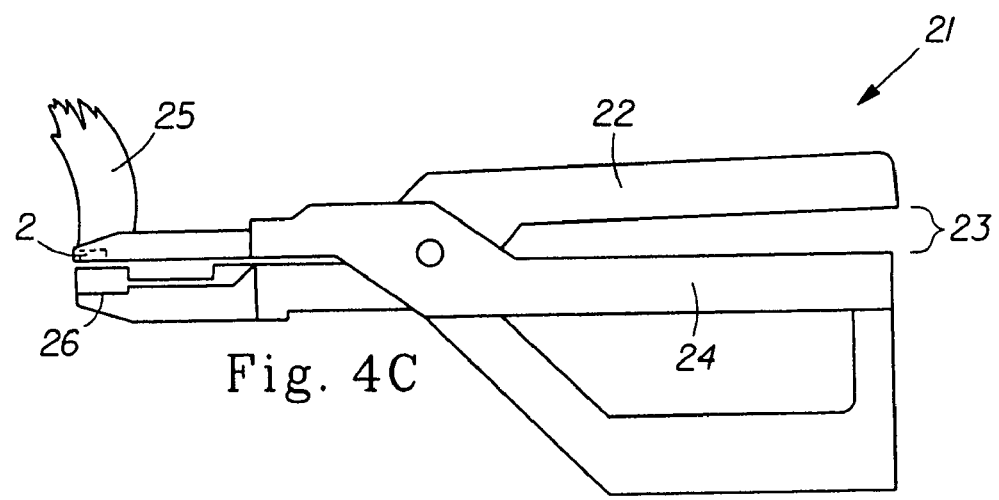
FIG. 4C is a view similar to FIG. 4B, illustrating the clamping device in a closed position to clamp hair in the device.

Referring now to FIGS. 4A, 4B and 4C, use of the sensor 1 to determine the moisture content of hair will now be described in connection with a hair moisture sensor system 20. The hair moisture sensor system 20 may be used by a professional salon, for example, to quickly, accurately, and reliably indicate to a stylist when the moisture content of a customer's hair is in the range of approximately 30% by weight to 40% by weight so that the optimum styling results may then be achieved. A hair clamping device 21 may be connected to a computer 27 via a device connection means 17, and moisture/hair health results may be displayed on the computer screen 28. As shown in FIGS. 4B and 4C, a hair clamping device 21 is provided having pivoted jaws 22a and 24a that each terminate in handles 22 and 24, that may be defined as opened or closed based on the distance therebetween 23. The jaws 22a and 24a may be biased to an open position as shown in FIG. 4B so that a bundle of hair 25 is readily received between the jaws 22a, 24a and is oriented with the hair fibers 25 extending across, i.e., generally normal to the longitudinal axis of, the coupling gap 5 (FIG. 3A) of the directional coupler 2 which is supported by jaw 24. The device may also incorporate a substrate packing means 26, which may comprise a gap, teeth, tines, or another structure which enables hair to be packed in a space between the directional coupler 2 and the packing means 26. A packing means 26 comprising a gap is preferred to aid in root to tip profile measurements.

In one application, the sensor 1 provides a consumer friendly self-assessment tool that permits a consumer to periodically measure the general health of the consumer's hair. Based on these measurements, the consumer is able to take corrective actions as necessary which tend to improve the health of the consumer's hair. These actions may include changing hair care products, changing hair styling techniques, or both, so that the general health of the consumer's hair can be consistently monitored and improved. The sensor 1 also provides a useful monitoring tool to hair stylists and hair technicians as well.

While not shown, it will be appreciated that the sensor 1 of the present invention may be incorporated into other hair care products as well, such as a comb, brush, curling iron, or similar hair care product that preferably engages the user's hair during grooming to provide a measurement of the moisture content, health or other status of the hair based on appliance function on hair. Generally, the health of hair is characterized by such factors as smoothness, shine, absence of fragility, absence of fissuring, and absence of cuticular breakdown. As each of these factors is directly or indirectly related to the moisture content of the hair, the sensor 1 of the present invention is able to provide an accurate and reliable indication of the health of measured in vivo or in vitro hair.

The directional coupler sensor 1 is well suited to measure the moisture content, health or other condition of hair since it possesses sensitivity to variations in impedance in close proximity, such as about 0.1 in., to the surfaces of the strips 3 and 4. The height of this effective measurement probing depth from the surfaces of the strips 3, 4 is a function of the electromagnetic field that couples the strips 3 and 4. The height of the measurement probing depth may be changed for a particular application by changing the height of the PCB 18, the dielectric constant of the PCB 18, the dimensions of the strips 3, 4, the coupling gap distance "s," and/or the power supplied by the signal generator 7. By varying any or all of these parameters, the height of the coupling field can be altered to thereby change the effective measurement probing depth.

It is contemplated that sensor 1 may comprise multiple directional couplers 2 electrically coupled to at least one signal generator 7 to measure the respective moisture content of multiple substrates in accordance with the principles described in detail above. It is further contemplated that at least two of the multiple directional couplers 2 may have different effective measurement probing depths by varying one or more of the parameters described in detail above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sensor for measuring moisture content of a substrate, comprising:
   (a) a signal generator operating in the VHF, UHF or microwave range, from which a signal at a chosen operating frequency is generated;
   (b) a directional coupler comprising two strips, a first strip and a second strip, wherein the first strip is generally parallel to the second strip such that a coupling gap is defined therebetween, wherein the substrate to be measured is placed across the coupling gap, the first strip being electrically coupled to the signal generator; and the first strip generating an electromagnetic field across the coupling gap to the second strip,
(c) the first strip is electrically coupled to a first port of a mixer;
(d) the second strip is electrically coupled to a section of coplanar waveguide, wherein the section of coplanar waveguide is designed to give a 90 degree phase shift to the signal at the chosen operating frequency, and the coplanar waveguide is electrically coupled to a second port of the mixer;
(e) the output of the mixer is electrically coupled to a computer with a visual display capable of a user-perceptible indication of the measured moisture content of the substrate; wherein the signal generator, the coplanar waveguide, and the mixer are integrated into a printed circuit board.

2. The sensor for measuring moisture content of a substrate of claim 1 wherein the coupling gap is 0.020 inches.

3. The sensor for measuring moisture content of a substrate of claim 1 wherein the printed circuit board is a Rogers board or a FR4 type board.

* * * * *